United States Patent
Harms et al.

(10) Patent No.: US 7,621,912 B2
(45) Date of Patent: Nov. 24, 2009

(54) ROD-SHAPED IMPLANT ELEMENT WITH FLEXIBLE SECTION

(75) Inventors: Jürgen Harms, Karlsruhe (DE); Lutz Biedermann, VS-Villingen (DE); Wilfried Matthis, Weisweil (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 454 days.

(21) Appl. No.: 10/966,921

(22) Filed: Oct. 15, 2004

(65) Prior Publication Data
US 2005/0085815 A1    Apr. 21, 2005

Related U.S. Application Data

(60) Provisional application No. 60/512,113, filed on Oct. 17, 2003, provisional application No. 60/518,469, filed on Nov. 7, 2003.

(30) Foreign Application Priority Data
Oct. 17, 2003    (DE) ................. 103 48 329

(51) Int. Cl.
    A61B 17/64    (2006.01)
    A61B 17/70    (2006.01)
(52) U.S. Cl. .................... 606/59; 606/246; 606/279
(58) Field of Classification Search .......... 606/60, 606/61, 72, 73, 59, 90, 105, 246, 254, 255, 606/257, 259, 261, 263, 264, 265, 266, 267, 606/270, 272, 279, 300, 301, 305; 623/17.13, 623/17.16
See application file for complete search history.

(56) References Cited

U.S. PATENT DOCUMENTS

| | | | |
|---|---|---|---|
| 5,306,310 A | 4/1994 | Siebels | |
| 5,320,644 A * | 6/1994 | Baumgartner | 623/17.16 |
| 5,423,816 A | 6/1995 | Lin | |
| 5,423,817 A | 6/1995 | Lin | |
| 5,486,174 A | 1/1996 | Fournet-Fayard et al. | |
| 5,672,175 A * | 9/1997 | Martin | 606/61 |
| 6,162,223 A | 12/2000 | Orsak et al. | |
| 6,402,750 B1 | 6/2002 | Atkinson et al. | |
| 6,770,094 B2 | 8/2004 | Fehling et al. | |

(Continued)

FOREIGN PATENT DOCUMENTS

EP    0 529 275 A2    3/1993

(Continued)

OTHER PUBLICATIONS

European Search Report dated Jan. 24, 2005 for Application No. EP 04 02 4539.

(Continued)

*Primary Examiner*—Eduardo C Robert
*Assistant Examiner*—David Comstock
(74) *Attorney, Agent, or Firm*—Christie, Parker & Hale, LLP (57) ABSTRACT

A rod-shaped implant element for the connection of bone anchoring elements includes at least one rigid section that is configured to be placed in a receiver member of a bone anchoring element and a flexible section that is adjacent to the rigid section. The flexible section and the rigid section are formed as a continuous one-piece element.

22 Claims, 9 Drawing Sheets

U.S. PATENT DOCUMENTS

| | | |
|---|---|---|
| 2002/0035366 A1 | 3/2002 | Walder et al. |
| 2003/0109880 A1 | 6/2003 | Shirado et al. |
| 2003/0171749 A1 | 9/2003 | Le Couedic et al. |
| 2003/0191470 A1 | 10/2003 | Ritland |
| 2003/0220643 A1 | 11/2003 | Ferree |
| 2005/0056979 A1 | 3/2005 | Studer et al. |
| 2005/0065514 A1 | 3/2005 | Studer |

FOREIGN PATENT DOCUMENTS

| | | |
|---|---|---|
| EP | 0 669 109 A1 | 8/1995 |
| EP | 0677277 | 10/1995 |
| EP | 0669 109 B1 | 5/1999 |
| EP | 0 950 389 A2 | 10/1999 |
| EP | 1 188 416 A1 | 3/2002 |
| EP | 1 273 276 A2 | 1/2003 |
| FR | 2 634 371 | 1/1990 |
| FR | 2 702 361 | 9/1994 |
| FR | 2702361 | 9/1994 |
| FR | 2 717 370 | 9/1995 |
| GB | 2382304 A | 5/2003 |
| JP | 5-45637 | 6/1993 |
| WO | WO 95/19153 | 7/1995 |
| WO | WO 96/15729 | 5/1996 |
| WO | WO96/15729 A1 | 5/1996 |
| WO | WO 96/16608 | 6/1996 |
| WO | WO 99/65425 | 12/1999 |
| WO | WO 02/07621 A1 | 1/2002 |
| WO | WO 03/047442 A1 | 6/2003 |
| WO | WO 2004/105577 A2 | 12/2004 |

OTHER PUBLICATIONS

Partial International Search Report dated Mar. 11, 2005 for Application No. PCT/EP2004/011782.

International Search Report dated May 18, 2005 for Application No. PCT/EP2004/011782.

European Search Report for Application EP 07 00 6072 completed Apr. 12, 2007 (9 pages) and mailed May 5, 2007.

English translation of Japanese Office Action for Patent Application No. 301448/2004, mailed Aug. 25, 2009, 2 sheets.

* cited by examiner

ROD-SHAPED IMPLANT ELEMENT WITH FLEXIBLE SECTION

CROSS REFERENCE TO RELATED APPLICATIONS

This application claim priority from U.S. Provisional Application Ser. No. 60/512,113 filed Oct. 17, 2003 and from U.S. Provisional Application Ser. No. 60/518,469 filed Nov. 7, 2003.

FIELD OF THE INVENTION

The present invention relates to a rod-shaped implant element for application in spine surgery or trauma surgery, a stabilization apparatus comprising said rod-shaped implant element, and a production method for such a rod-shaped implant element In particular, the rod-shaped implant element has an integral flexible section.

BACKGROUND OF THE INVENTION

EP 0 669 109 B1 discloses a stabilization apparatus for stabilizing neighboring thoracic vertebrae, which comprises two monoaxial pedicle screws and a strap that is fixed in the receiver members of each pedicle screw by means of a clamping screw and which contains a support element that is mounted on the strap and is designed as a pressure-resistant body. However, this stabilization apparatus fails to be torsionally stiff. In addition, the use of monoaxial pedicle screws limits the application of this stabilization apparatus. A similar stabilization apparatus where polyaxial pedicle screws are used instead of monoaxial pedicle screws is known from EP 1 188 416 A1.

A joint fixation apparatus, for example for a wrist or a knee joint, is disclosed in U.S. Pat. No. 6,162,223. The apparatus comprises a fixation rod that is connected to bone anchoring elements at its ends and consists of two parts, wherein the two parts of the fixation rod are connected to one another via a flexible coupling and wherein the fixation rods and the coupling are arranged outside of the body. The ends of the two parts of the fixation rod that are facing each other are designed hemispherically and abut against each other, thus simulating a type of joint whose freedom of movement is limited by the flexible coupling. Owing to its complex and voluminous structure, this known joint fixation apparatus is not suitable for being used on the spinal column.

US 2003/0109880 A1 discloses a dynamic stabilization apparatus for vertebrae, which comprises first and second screws to be anchored in the vertebra, with each screw being provided with a receiver member for insertion of a coil spring that connects the screws. The spring itself, as a whole, is designed in the form of a coil spring with closely adjacent windings, similar to a tension spring, and is fixed in the receiver members by means of clamping screws. This, however, poses the risk that the spring, owing to its flexibility, evades the pressure of the clamping screw, thus causing the fixation between the bone screw and the spring to loosen.

US 2003/0220643A1 discloses a stretchable element to be used in an apparatus for preventing full extension between upper and lower vertebral bodies. The stretchable element may be, for example, an elastic cord or a spring.

US 2003/0191470A1 discloses an implant device having a rod portion with a center section that flexes when the patient bends their spine. The flexible section can be a linear rod having a variable cross-sectional shape or a non-linear rod having a portion bent in a U-like shape to one side of the axis similar to expansion sections in pipes undergoing temperature changes.

There remains a need for compact implant devices that permit the stabilization and limited movement of vertebrae or bones that are to be connected to each other.

SUMMARY OF THE INVENTION

The present invention provides a rod-shaped implant element for the stabilization and limited movement of vertebrae or bones that are to be connected to each other. In accord with preferred embodiments of the present invention, the rod-shaped implant element has a simple and compact design, can be handled easily and can be used in manifold ways, at the same time providing high reliability in use.

The invention also provides a dynamic stabilization apparatus of compact design that uses such a rod-shaped implant element and methods for production of the rod-shaped implant element.

Thus, the invention provides an elongated rod-shaped implant element for connecting at least two bone anchoring elements, each of which comprises an anchoring section to be anchored ill the bone and a receiver member to be connected to the rod-shaped implant element, the elongated rod-shaped implant element comprising: a longitudinal axis and an outer surface; at least one first length of a rigid section that is configured to cooperate with and be received in the receiver member; and a second length of a flexible section adjacent to the rigid section, the second length having, a helical slotted opening in the outer surface of the rod-shaped implant element, the slot extending radially inward, wherein the rigid section and the flexible section are a continuous one-piece element.

In certain preferred embodiments of the invention, the rod-shaped implant element further comprises one or more of the following:

a coaxial longitudinal bore extending throughout the element;

a third length of a rigid section, and wherein the flexible section has two opposite ends, the first length of rigid section being adjacent a first end and the third length of rigid section being adjacent the opposite second end;

the flexible section has a first diameter and the rigid section has at least at one point a second diameter different from the first diameter;

the flexible section has two symmetrical concave surfaces in the outer surface, the concavity being an arcuate shape the arc of which extends along the longitudinal axis;

the flexible section has an outer diameter that varies along a length of the flexible section;

the flexible section further comprising a core;

the rod-shaped implant element comprises a first material and the core comprises a second material;

the core has at least in a part of the flexible section a cross section with an anisotropic shape; and the core is accommodated in the bore with a tolerance in direction of the longitudinal axis;

The invention also provides a stabilization apparatus for bones comprising at least two bone anchoring elements and a rod-shaped implant element connecting the bone anchoring elements, wherein each bone anchoring element comprising a bone anchoring section to be anchored in the bone and a receiver member for receiving the rod-shaped implant element, and wherein the rod-shaped implant element is as described herein.

A method for making the rod-shaped implant element having a flexible section also is provided The method comprises the following steps: providing a rigid rod; and producing a helical slotted opening in at least one section of the outer surface of the rod at a predefined distance from a free end of the rod, thereby providing the flexible section.

In addition, the invention provides methods for stabilizing two sections of bone or two vertebrae. In a patient in need of bone or vertebrae stabilization, at least two bone anchoring elements are inserted into bone on opposite sides of a fracture, or break, or other instability, or on two adjacent vertebrae. Each bone anchoring element comprising a bone anchoring section to be anchored in the bone and a receiver member for receiving the rod-shaped implant element having a structure as described herein. The rod-shaped implant element is inserted and locked into the receiver member of the adjacent bone anchoring elements and the bone anchoring elements are hereby linked by a flexible element.

Preferred embodiments of the rod-shaped implant element of the present invention can absorb one or more of the axial forces, bending forces and torsional forces exerted by the patient. Further, the rod-shaped implant element of the present invention can be used with the known polyaxial or monoaxial bone screws and can be reliably fixed in position with such screws.

In particular, the rod-shaped implant element of the present invention is suitable for use for the stabilization and limited movement of adjacent vertebrae in case of defects of the intervertebral disks of various degrees of severity. These characteristics for use in connection with various degrees of severity can be easily realized during production, by changing the dimensions of the various sections of the integral rod-shaped implant element.

Further features and benefits of the invention are evident to those skilled in the art by the description of the embodiments by means of the Figures and discussion that follows.

BRIEF DESCRIPTION OF THE DRAWINGS

FIG. 4b is a sectional view of the connection between the rod-shaped implant element and the bone anchoring elements of FIG. 4a;

FIG. 19a shows a perspective view of a seventh embodiment of the rod-shaped implant element in accord with the present invention;

FIG. 19b shows a side view of the rod-shaped implant element FIG. 19a;

FIG. 19c shows a sectional view of the rod-shaped implant element of FIG. 19a along the rod axis;

FIG. 20a shows an enlarged view of the lower part of FIG. 19c; and

FIG. 20b shows a perspective view of a detail of the rod-shaped implant element of FIG. 20a.

DETAILED DESCRIPTION OF THE INVENTION

Figure 1:
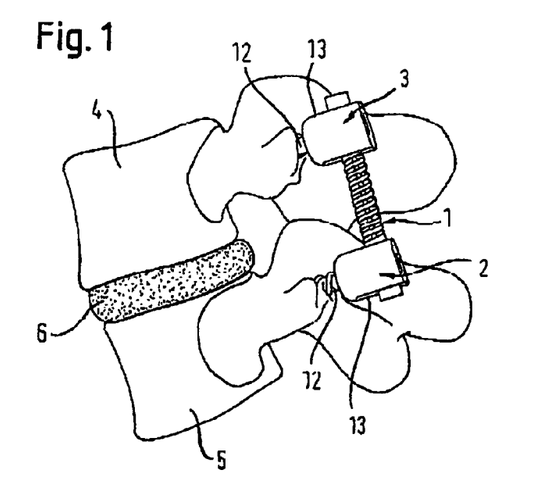
FIG. 1 is a schematic perspective view of one embodiment of a stabilization apparatus according to the invention, comprising a rod-shaped implant element, in a first application.

As can be seen from FIG. 1, in accord with the present invention, one embodiment of a stabilization apparatus comprises in a first application a rod-shaped implant element 1 and two pedicle screws 2, 3, which are connected to one another by means of the rod-shaped implant element. The pedicle screws 2, 3 are anchored in the pedicles of two adjacent vertebrae 4, 5 which enclose between them a damaged intervertebral disk 6.

Figure 2:
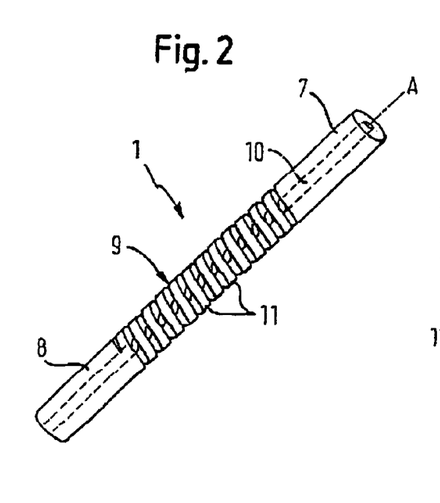
FIG. 2 shows in perspective a rod-shaped implant element according to a first embodiment of the invention.
Figure 3A:
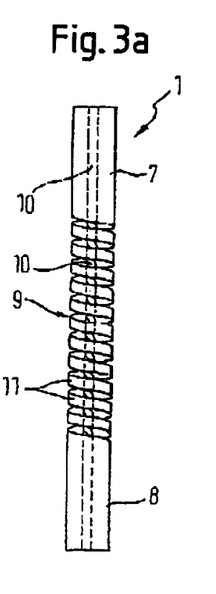
FIG. 3a is a lateral view of the rod-shaped implant element of FIG. 2.
Figure 3B:
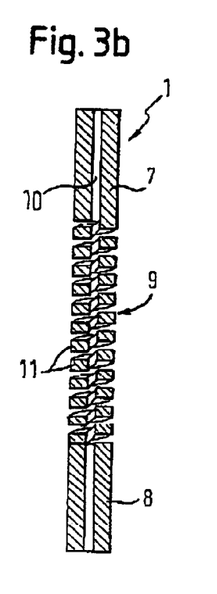
FIG. 3b is a sectional view of the rod-shaped implant element of FIG. 2.

The rod-shaped implant element 1 according to the invention is designed as a single piece. As shown in FIGS. 2, 3a and 3b, the rod-shaped implant element comprises in a first embodiment a first rigid section 7 that extends across a predefined length from its first end and a second rigid section 8 that extends across a predefined length from its second end as well as a flexible section 9 of predefined length that is provided between the rigid sections 7, 8, with all sections having the same outside diameter. In addition, a coaxial bore 10 of predefined diameter extends through the rod-shaped implant element, The flexible section 9 is designed with a helical slotted opening extending radially from the surface to the coaxial bore 10 with windings 11 of a predefined pitch (a helical groove). The groove can have straight or tap end sides. The height of the windings 11 of the flexible section 9 in the direction of the longitudinal axis A of the rod-shaped implant element, the diameter of the coaxial bore 10 that defines the thickness of the windings 11 in radial direction, as well as the pitch are selected such that a desired stiffness towards axial forces, bending forces and torsional forces that are acting on the rod-shaped implant element 1 can be obtained. These dimensions can be varied readily by those skilled in the art to achieve the desired stiffness without undue experimentation.

Figure 4A:
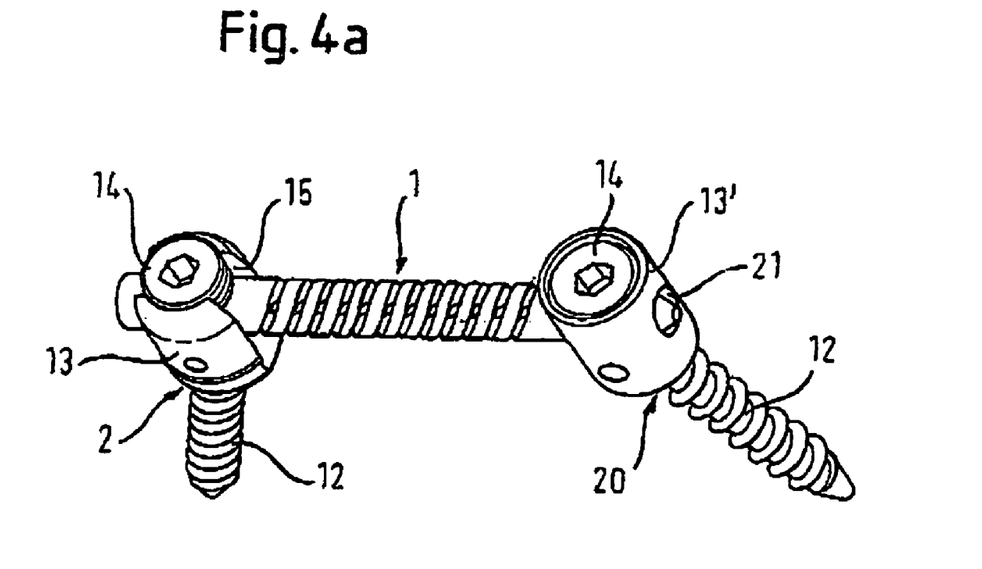
FIG. 4a shows in perspective the connection between a rod-shaped implant element in accord with the invention and two bone anchoring elements.
Figure 4B:
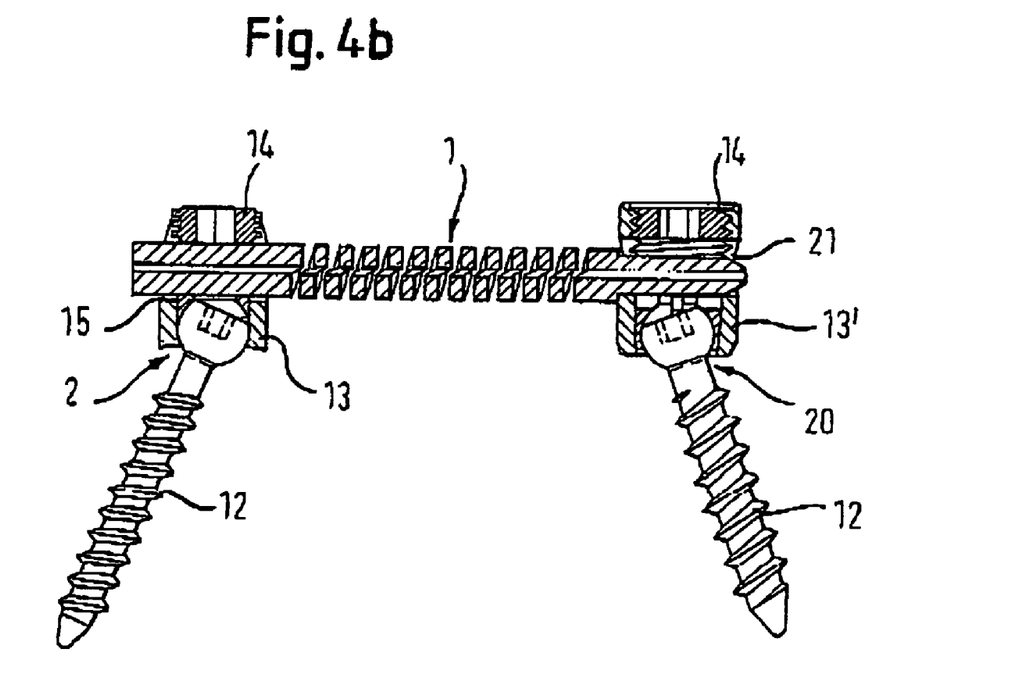

As can be seen from FIG. 1, FIG. 4a and FIG. 4b, a pedicle screw 2, 3 of the stabilization apparatus comprises, in known manner, a threaded shank 12 with a bone thread and an essentially cylindrical receiver member 13 with a U-shaped recess 15 for insertion of the rod-shaped implant element. Internal screws 14 that can be screwed into the receiver member 13 in known manner are provided to fix the rigid sections 7, 8 in the receiver member 13. Preferably, the pedicle screws are designed as polyaxial screws. The axial length and the diameter of the rigid sections 7, 8 of the rod-shaped implant element are dimensioned such that the rod-shaped implant element 1 can be connected to the pedicle screws 2, 3 with its rigid sections 7, 8. Hence, the length of the rigid sections 7, 8 corresponds approximately to at least the diameter of the internal screw 14 that is provided for fixing the rod-shaped implant element. If a pedicle screw 20 is provided with receiver members 13' where the rod-shaped implant element is not inserted from above but is pushed laterally into an opening 21, the length of the rigid section likewise preferably corresponds approximately to at least the diameter of the fixing element 14 that fixes the rod-shaped implant element in the receiver member 13'.

In the example of the stabilization apparatus shown in FIG. 1, the length of the flexible section 9 of the rod-shaped implant element 1 is selected such that it essentially corresponds to the distance between the pedicle screws 2, 3, with the intervertebral disk 6 not being under stress. However, the flexible section 9 also can be shorter or longer.

The rod-shaped implant element 1 is made of a biocompatible material, for example, such as titanium, or as a biocompatible plastic material not having any, or having only, weak elastomeric properties.

During operation, the pedicle screws 2, 3, 20 are first screwed into the pedicles of adjacent vertebrae and then, with its rigid sections 7, 8, the rod-shaped implant element 1 is inserted into each one of the receiver members 13, 13' of the pedicle screws 2, 3, 20. After the vertebrae 4, 5 have been positioned in relation to each other and the pedicle screws 2, 3, 20 have been adjusted in relation to the rod-shaped implant element, the rigid sections 7, 8 are fixed in the receiver members 13, 13'. In one application, the vertebrae 4, 5 are positioned in relation to each other such that the flexible section 9 of the rod-shaped implant element 1 is in the rest position with the intervertebral disk 6 not being under stress. Under stress, forces are acting upon the intervertebral disk 6 via the vertebrae and the ligamentous apparatus. Via the flexible section 9, the rod-shaped implant element 1 limits the multi-axial motion of the vertebrae in relation to each other, thus preventing extremely strong forces from acting on the intervertebral disk 6. In this manner, it is possible to stop the degeneration process of an intervertebral disk that is defective to a minor or moderate degree. Alternatively, and depending on the particular indication, the stabilization apparatus is used to already achieve a predefined distraction of the vertebrae when the spinal column is not under stress, in order to relieve the intervertebral disk. Alternatively, and also depending on the particular indication, bone screws can be directly anchored laterally in the vertebral bodies.

Figure 5:
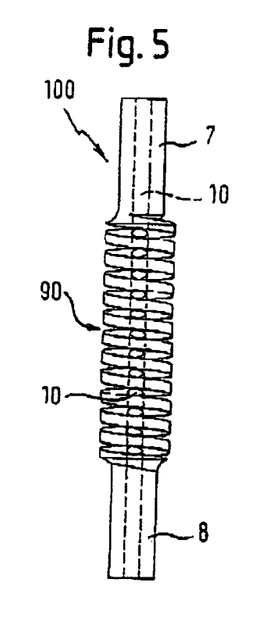
FIG. 5 is a lateral view of a rod-shaped implant element according to a second embodiment of the invention.

In the second embodiment that is shown in FIG. 5, a rod-shaped implant element 100 comprises the rigid sections 7, 8 (as in the first embodiment), as well as a flexible section 90 that is designed as a helical slotted radially extending opening adjacent to the rigid sections 7, 8 in a single piece and is arranged between the rigid sections 7, 8. It is different from the first embodiment in that the diameter of the flexible section 90 exceeds the diameter of the rigid sections 7, 8. As a result, the stiffness obtained is higher than the stiffness of the rod-shaped implant element according to the first embodiment. The operation is identical with the first embodiment.

Figure 6:
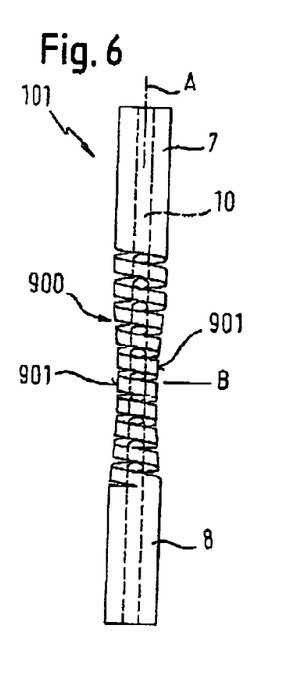
FIG. 6 is a lateral view of a rod-shaped implant element according to a third embodiment of the invention.
Figure 7:
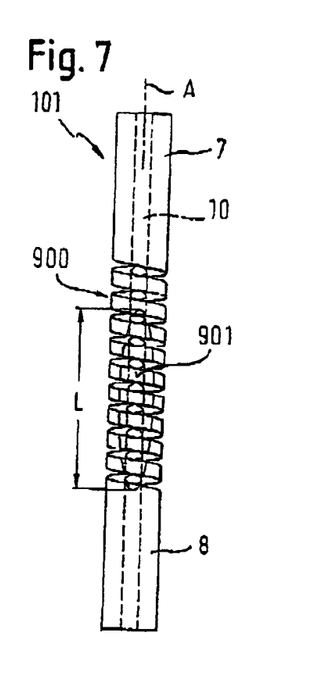
FIG. 7 is a lateral view of the rod-shaped implant element of FIG. 6, turned by 90 degrees.

FIGS. 6 and 7 show a rod-shaped implant element 101 according to a third embodiment. This rod shaped implant element is different from the rod-shaped implant elements 1, 100 of the preceding embodiments in that the flexible section 900 that is provided between the rigid sections 7, 8 comprises two regions 901 that are offset by 180 degrees in relation to each other and are shaped towards the axis of the rod in a concave manner in an arc extending along the axis. The length L of the regions 901 in direction of the rod axis is no more than equal to the length of the flexible section 901, and the bending radius is such that the windings of the helical slotted openings are not interrupted. Due to this form, the flexible section 900 has a "waisted" form (i.e., like the waist of a person) in a direction B that is perpendicular to the rod axis A, thus possessing less stiffness in this direction. This provides an oriented stiffness that is appropriate for certain applications.

The operation is identical with the first and second embodiments. The rod-shaped implant element 101 differs only in that it can be fixed in the pedicle screws and oriented in circumferential direction due to regions 901. By selecting the dimensions of the flexible section, a desired stiffness can be selected and adjusted in a precise manner.

Figure 8:
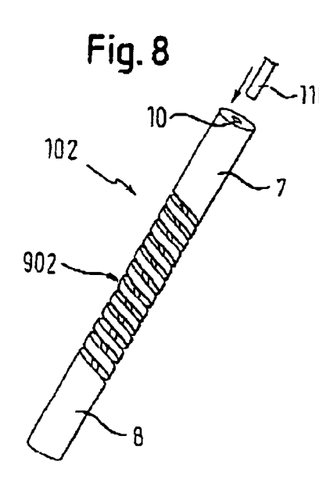
FIG. 8 shows in perspective a rod-shaped implant element according to a fourth embodiment of the invention.
Figure 9:
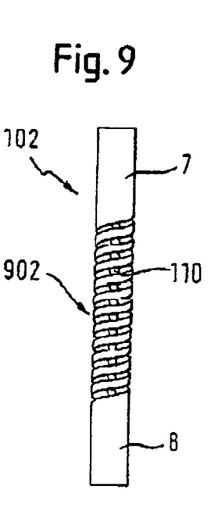
FIG. 9 is a lateral view of the rod-shaped implant element according to Fig, 8.

In a fourth embodiment that is shown in FIG. 8 and 9, the rod-shaped implant element 102 comprises a cylindrical core 110 that extends in coaxial direction through the flexible section 902 and possesses a specific bending flexibility. The diameter of the core 110 is dimensioned such that the core 110, after having been pushed into the bore 10, is truly secured in the latter. Preferably, the core is made of the same material as the rod-shaped implant element, but it may also consist of a second biocompatible material. such as, for example, a flexible plastic material.

In a modified form, the core 110 is connected to the rigid sections 7, 8 and to the windings of the helical slot flexible section 902 in a single piece. For example, when a core of the same material is desired, it also can be provided by omitting the coaxial bore in the manufacturing of the rod-shaped implant element. As compared with the first embodiment, the core 110 causes a higher bending stiffness of the rod-shaped implant element 102. In this embodiment, a stiffness can be obtained that is similar to that of the rod-shaped implant element 100 of the second embodiment, that comprises the larger diameter of the flexible section. Moreover, the bending stiffness can be adjusted by selecting the diameter, shape and/or the material of the core. A shape memory alloy can also be used, for example, which has the known characteristic of superelasticity.

Again, the operation is identical with the preceding embodiments. As a difference from the preceding embodiments, however, compression and/or extension of the flexible section 902 in axial direction as well as a torsion is reduced according to the specific dimensions. In the case of this embodiment, preferably only flectional movements are admitted, this being of advantage for certain applications.

Figure 10:
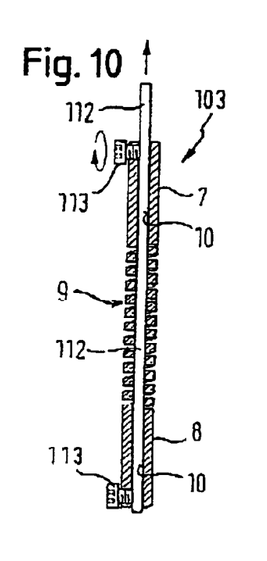
FIG. 10 is a sectional view of the rod-shaped implant element according to a fifth embodiment of the invention.
Figures 11, 12:
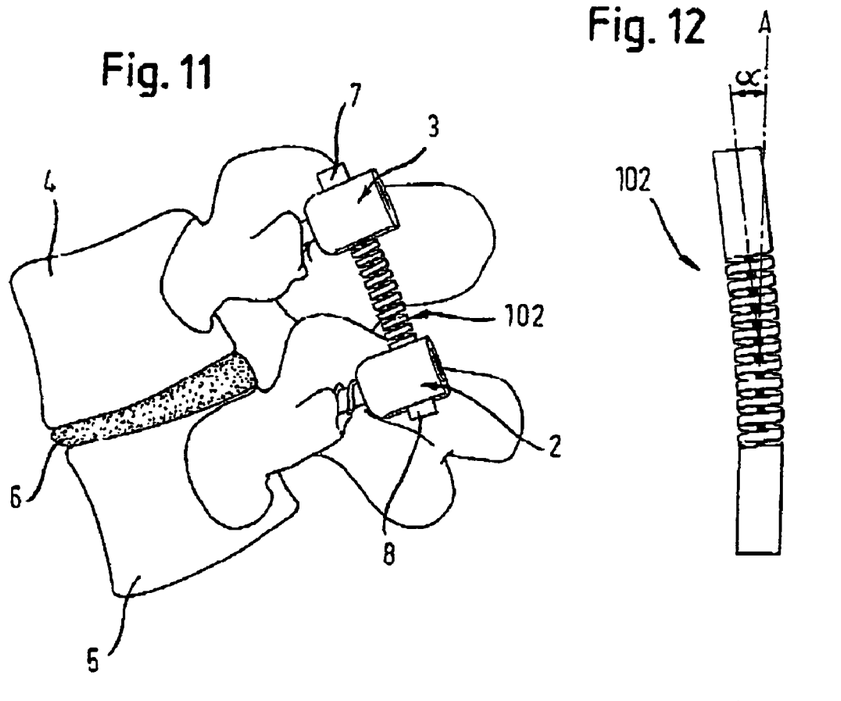
FIG. 11 shows in perspective the stabilization apparatus according to the invention comprising the rod-shaped implant element according to the fourth embodiment in a first state of two vertebrae.
FIG. 12 is a lateral view of the rod-shaped implant element according to FIG. 11 in the first state.
Figure 13:
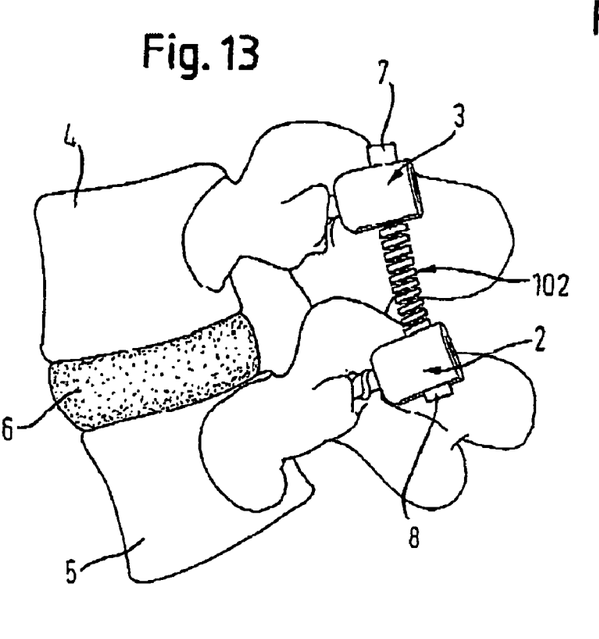
FIG. 13 shows in perspective the stabilization apparatus according to the invention comprising the rod-shaped implant element according to the fourth embodiment in a second state of two vertebrae.
Figure 14:
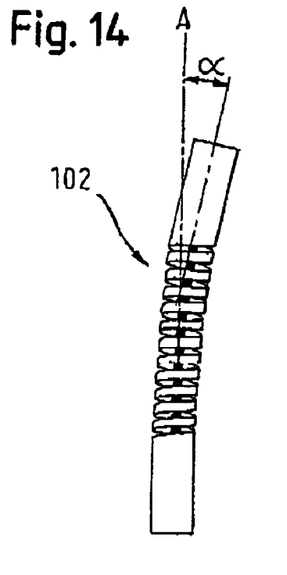
FIG. 14 is a lateral view of the rod-shaped implant element of FIG. 13 in the second state.

In a fifth embodiment that is shown in FIG. 10, the rod-shaped implant element 103 comprises the rigid sections 7, 8 and the flexible section 9, as is the case in the first embodiment. A pull element 112, for example a wire, is provided in the coaxial bore 10, which is preferably a coaxial bore, wherein this pull element is mounted under tension to the rigid sections 7, 8 by means of fixing elements, such as clamping screws 13. As a result, the flexible section 9 can be tensioned during application.

The features of the embodiments described above can be combined with each other. For example, the rod-shaped implant element of the second embodiment may also comprise a core and/or shaped sections in order to obtain an oriented stiffness. In a modified third embodiment, the flexible section can be uniformly waisted at one point, or in several regions that are uniformly spaced apart from each other in circumferential direction and are shaped in a concave manner to obtain a specific stiffness in defined directions.

In a further embodiment, the rod can comprise one or more rigid sections with one or more flexible sections respectively arranged so that a plurality of pedicle screws can, in this manner, be connected to each other, whereby this connection is in part rigid and in part flexible.

In a further embodiment, a coating or protective covering made of biocompatible material is provided around the flexible section, so as to ensure that tissue or blood vessels or other body material is prevented from entering the space between the windings and, thus, from being damaged or from affecting the proper function of the rod-shaped implant element.

In a further embodiment, polyaxial screws are provided instead of monoaxial screws, or a combination comprising a polyaxial screw and a monoaxial screw or combinations of several of these screws are used for the stabilization apparatus. It is even conceivable that bone hooks be used for particular applications instead of bone screws. In a further embodiment, the rigid sections and/or the flexible section are bent for a particular application where a straight rod cannot be accommodated.

FIGS. 11 to 17 show preferred applications of the stabilization apparatus comprising the rod-shaped implant element according to the invention. In the stabilization apparatus that is shown in FIGS. 11 to 14, use is made of the rod-shaped implant element according to the fourth embodiment, that is provided with the core 110. For example, this stabilization apparatus can be used if it is intended to support an intervertebral disk that is defective to a minor or moderate degree or to prevent harmful forces from acting on the intervertebral disk by limiting the movement of the vertebrae. The rod-shaped implant element 102 is rigid in axial direction and does not permit any compression or extension in axial direction. However, flectional movements across up to an angle α to the longitudinal axis of the rod, for example of up to ±8 degrees, are permitted. The angle α can be varied by varying the stiffness of the rod.

Figure 15:
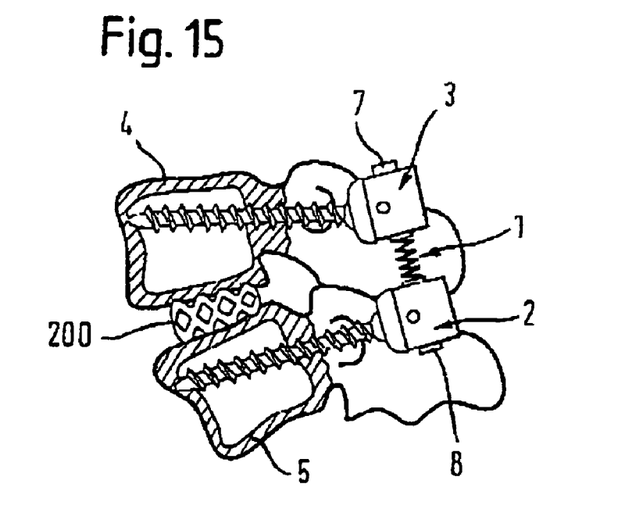
FIG. 15 shows a second application example of a stabilization apparatus in accord with the present invention.

FIG. 15 shows an application of the stabilization apparatus comprising the rod-shaped implant element, where two vertebrae 4, 5 are fused by means of a rigid element 200, for example a titanium cylinder, after the natural intervertebral disk has been removed. Here, a higher stiffness of the rod is desired, in order to obtain an adequate limitation of movement. The permitted possibility of the vertebrae for moving in relation to each other in this application, however, is an advantage as compared to a totally stiff connection, because the higher cyclical partial stress stimulates the growth of bone, thus accelerating the ossification process.

Figure 16:
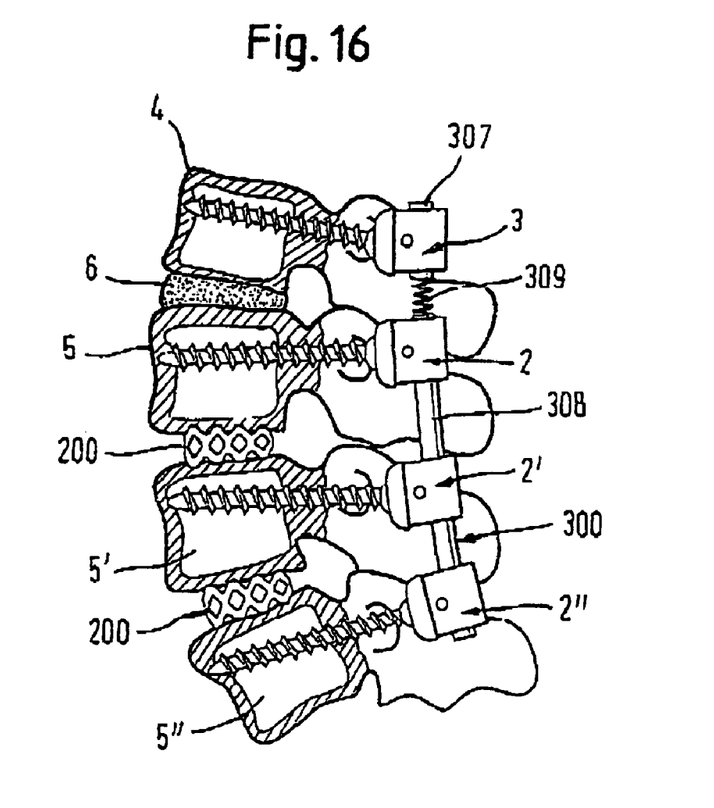
FIG. 16 shows a third application example of a stabilization apparatus in accord with the present invention.

FIG. 16 shows an application of the dynamic stabilization apparatus as the flexible end of a long-distance fusion, where several vertebrae, that are 5, 5', 5" in the example shown, are fused via rigid elements 200 and provided with a posterior connection via a rigid rod 300. The natural intervertebral disk 6 that is adjacent to the last vertebra 5 of the fusion chain as well as the following vertebra 4 are subject to above-average stress causing increased wear of the intervertebral disk 6. To protect this neighboring segment from unusual movements and, thus, increased stress, the stabilization apparatus is provided to limit movement. In this example, the rod 300 comprises a rigid section 308 that is dimensioned such that three pedicle screws 2, 2', 2" can be connected thereto; the flexible section 309 is provided adjacent thereto and between pedicle screws 2 and 3; and another rigid section 307 is, finally, provided to be connected to the pedicle screw 3.

Figure 17:
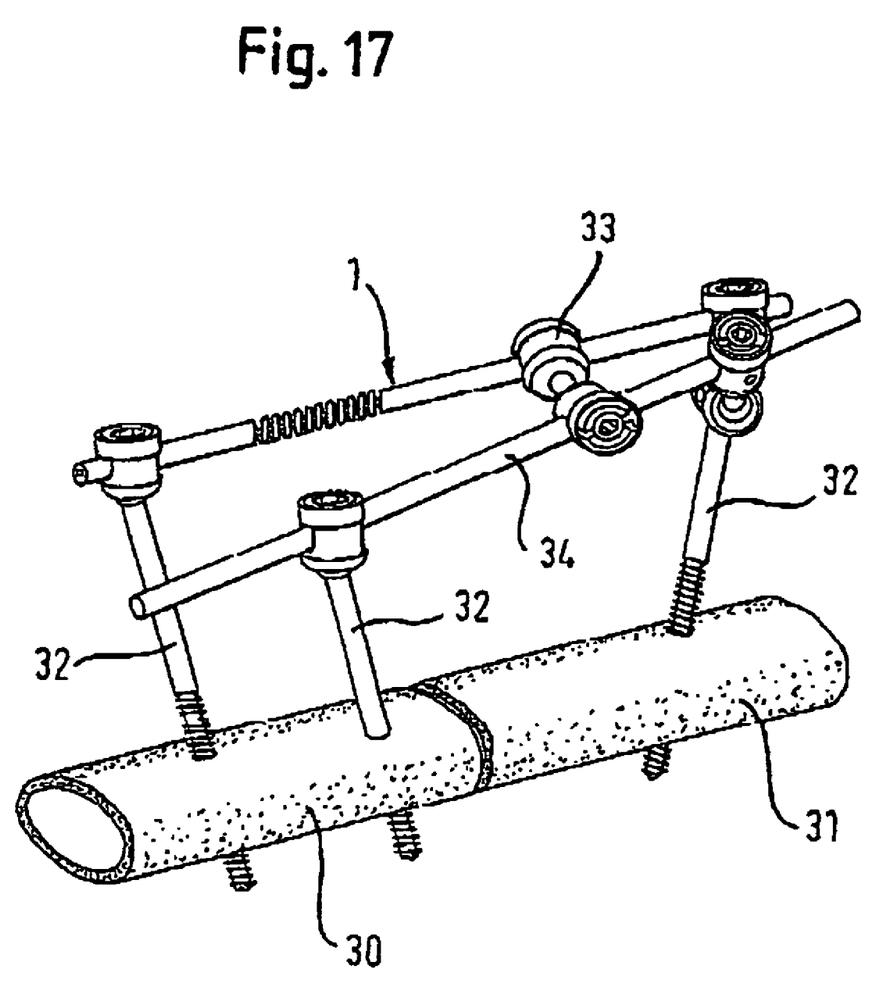
FIG. 17 shows in perspective a fourth application example of the stabilization apparatus in accord with the present invention.

FIG. 17 shows an example of application of the rod-shaped implant element 1 in a stabilization apparatus according to a fixateur externe for stabilizing, for example, long bones. Parts 30, 31 of the bone are stabilized by means of bone screws 32 which are, for example, connected to a rigid rod 34 and a rod shaped implant element 1 according to the invention via a connection element 33.

The rod-shaped implant element of the invention can be manufactured by providing a rigid rod of a desired diameter that is made of a body-compatible material, such as titanium. At a desired section between the ends of the rod, the flexible section 9, 900, 902 is then produced by generating a slotted opening in the form of a helix, for example by milling. Subsequently, if desired the central core 110 that extends through the spring section can be drilled out, whereby the rod having a coaxial bore according to the first embodiment is produced.

To produce the rod according to the fourth embodiment, the core 110 is either left in its place or a separate core is pushed in subsequently.

To produce the rod according to the second embodiment, a rod of a diameter that corresponds to the diameter of the desired flexible section 90 is provided as base material. Subsequently, the slotted helix opening is produced, for example by milling. Then the rigid end sections 7, 8 are turned down to the desired diameter.

To produce the rod according to the third embodiment, material is removed at points of the flexible section that are offset against each other by 180 degrees in circumferential direction, so as to produce an oriented "waist" section.

Figure 18:
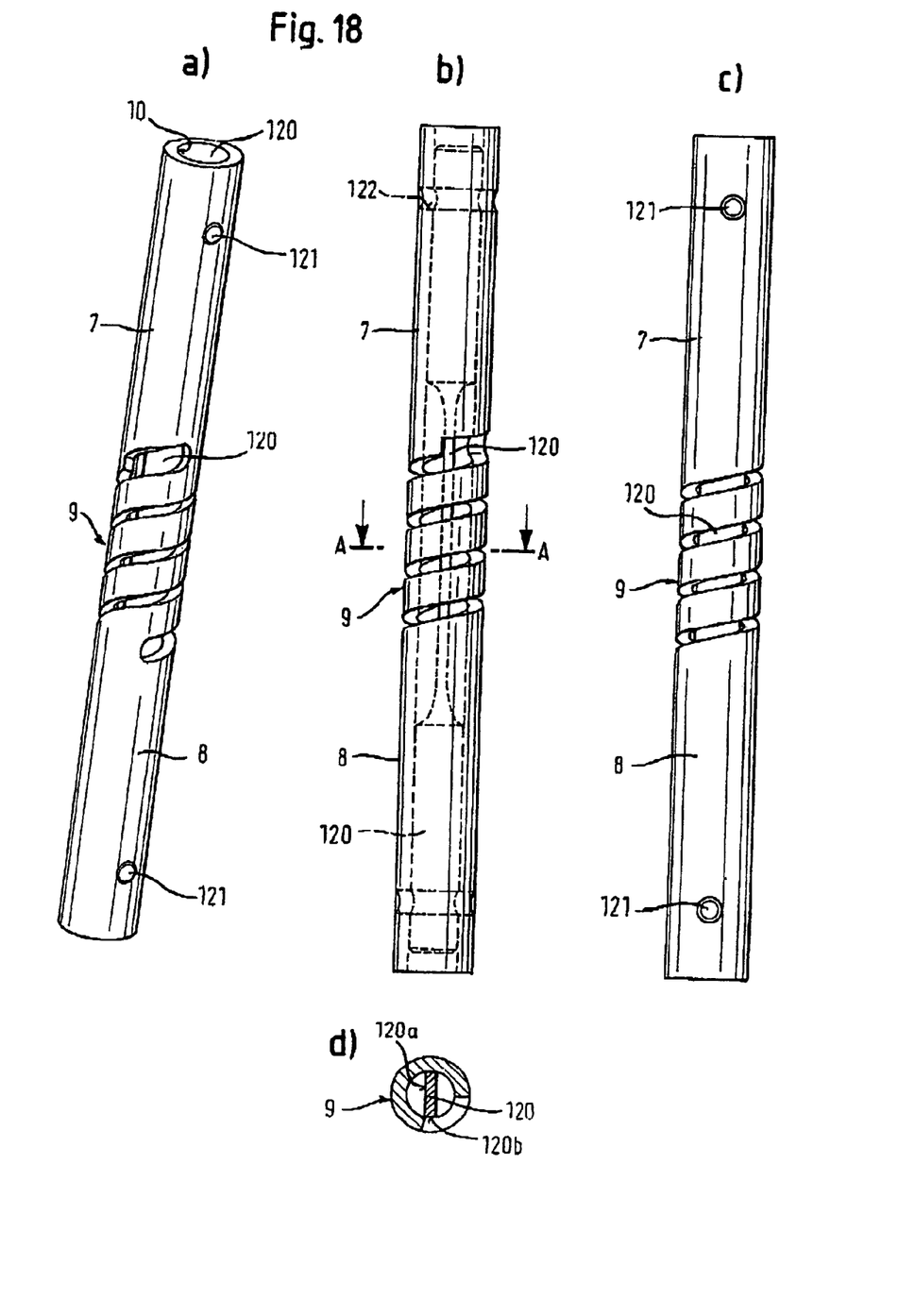
FIG. 18a shows a perspective view of a sixth embodiment of a rod-shaped implant element in accord with the present invention.
FIG. 18b shows a side view of the rod-shaped implant element of FIG. 18a with the interior part in dashed lines.
FIG. 18c shows a further side view of the rod-shaped implant element FIG. 18b tuned by 90°.
FIG. 18d shows a cross sectional view of the rod-shaped implant element perpendicular to the longitudinal axis in the flexible section along A-A in FIG. 18b.

A further embodiment of the invention is shown FIGS. 18a to 18d. In this embodiment the core 120 is formed to have a rectangular cross-section in a plane perpendicular to the rod axis for at least a part of the flexible section 9 (see FIG. 18d). Thereby, the rectangular cross-section is formed having a long side 120a and a short side 120b, as shown in FIG. 18d. Preferably, in the sections of the core 120 inside the rigid sections 7, 8, the core 120 has a circular cross-section adapted to the inner diameter of the bore 10 to facilitate fastening of the core as shown by the dashed line in FIG. 18b. Fastening can be achieved, for example, by a pin 121 extending through a traverse bore 122.

The rectangular planar shape of the core 120 in the region of the flexible section 9 has the effect of a high flexural stiffness of the rod-shaped implant element in the direction of the long side 120a of the rectangular cross-section and a low flexural stiffness in the direction of the short side 120b of the rectangular cross-section Thus, for special applications, a higher mobility is possible in one direction and a limited mobility in the perpendicular direction depending on the direction in which the core 120 is arranged. Compared to the embodiments having no core or a having a wire provided in the bore, the compressive and tensional strength are increased. The torsional stiffness can also be adjusted by selecting an appropriate core.

To achieve the desired effect, the section of the core does not need to have a rectangular cross-section, but other cross-sectional shapes as e.g. an oval cross-section, a basically rectangular cross-section having sides partially shaped concavely or convexly or even a triangular cross-section can be selected. It is important generally for the cross-section to have different dimensions in two perpendicular axes (or at least in two different directions) lying in the plane perpendicular to the rod axis. In this way, a direction-dependent flexural stiffness is achieved.

As in the other embodiments, the core 120 in this embodiment (depending upon the geometry) may be formed in one piece with the rod or may be formed separately and inserted into the rod. A combination of this core 120 with the other embodiments is also possible to adapt the characteristics of the rod-shaped implant element to special requirements.

Figure 19:
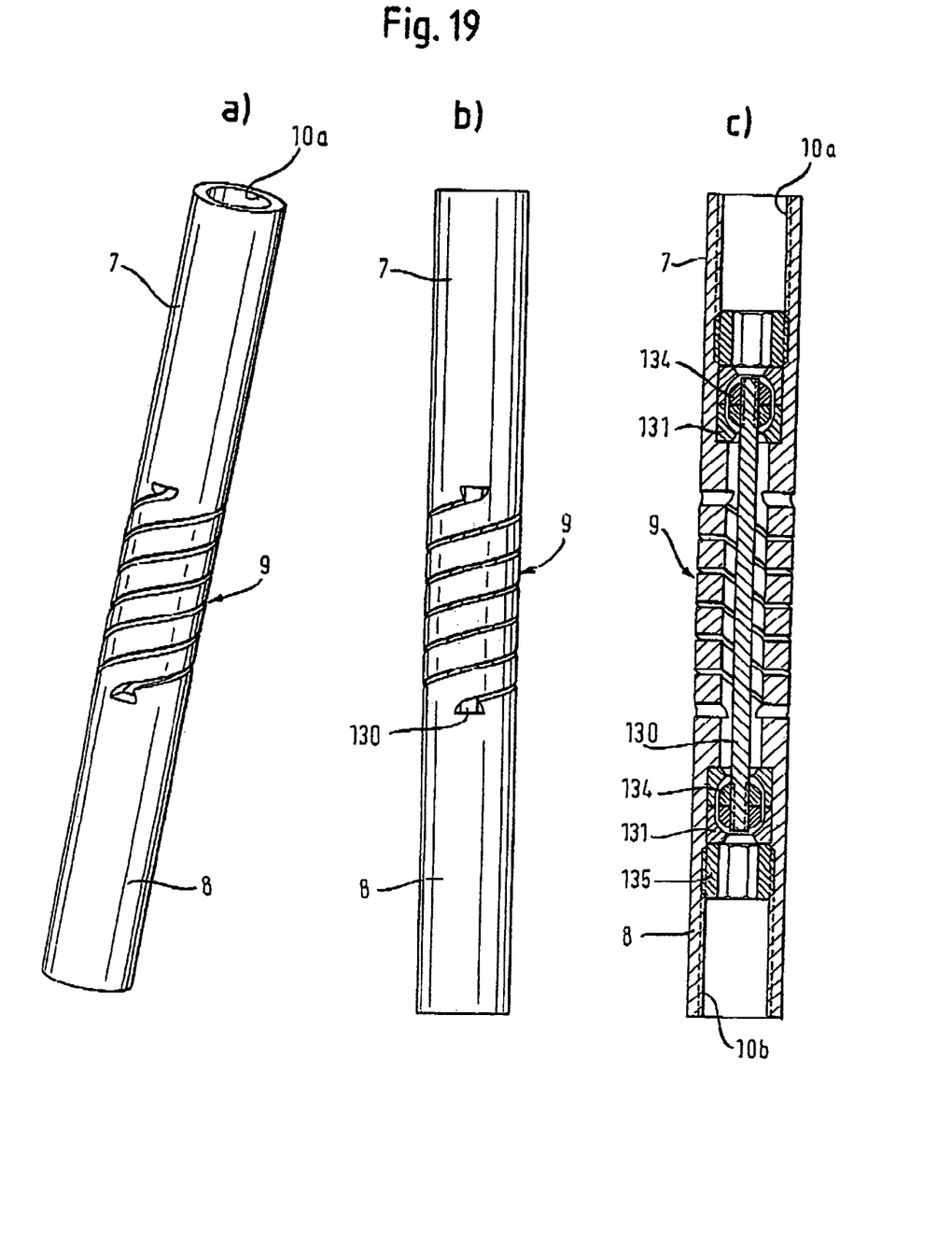

In the embodiment shown in FIGS. 19a to 19c and 20a and 20b, a special mounting is provided for the core. As particularly shown in FIG. 20a, adjacent to the bore 10 a second coaxial bore 10b is formed in the rigid section 8 in the direction of the free end. Similarly, coaxial bore 10a is formed in rigid section 7 (FIG. 19c). In the embodiment shown, the rigid sections 7, 8 are formed symmetrically on both sides of the flexible section 9, so that only the section 8 will be described referring to FIG. 20a.

Figure 20:
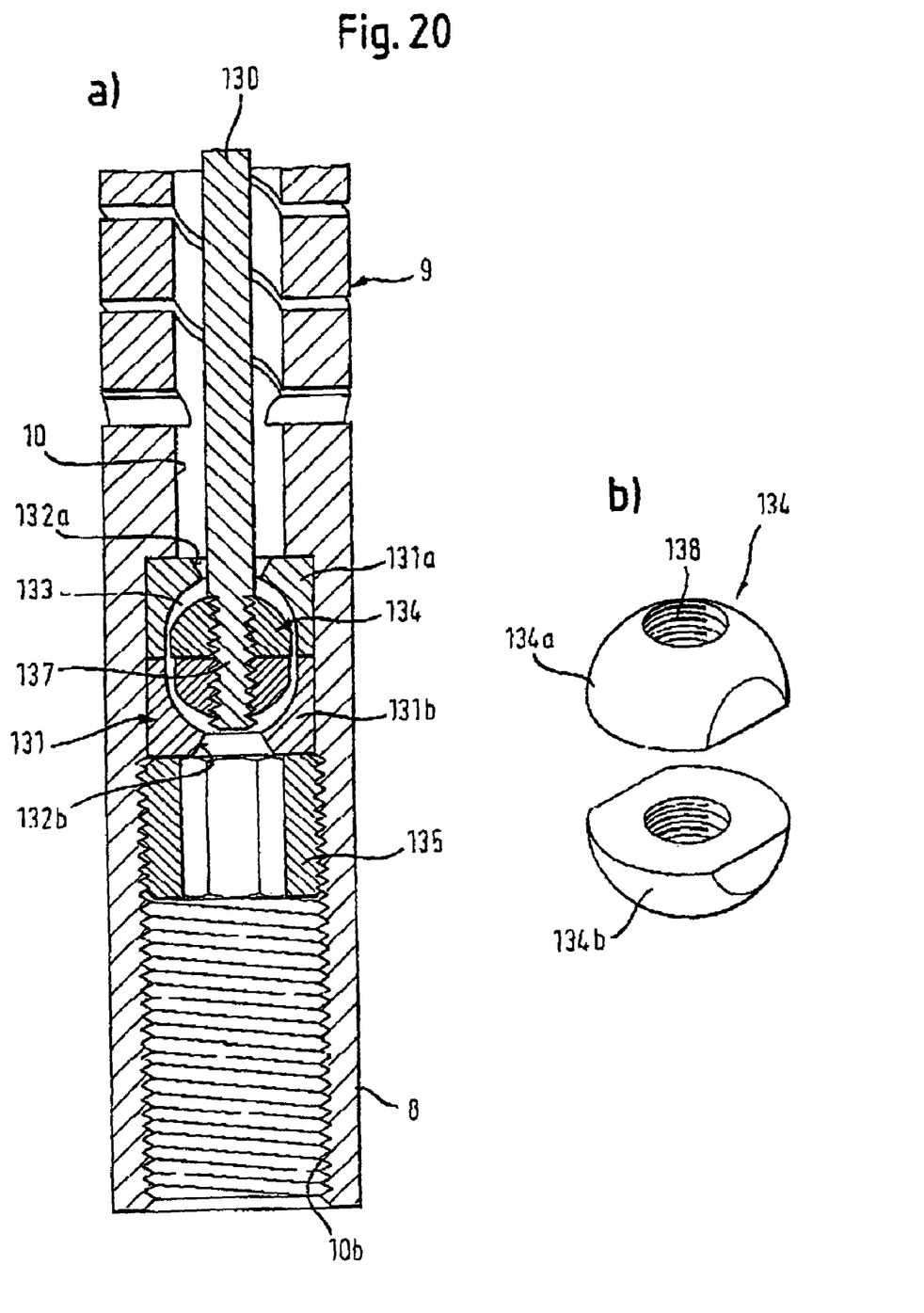

In the second bore 10b adjacent to bore 10 a head receiving member 131 is provided having an outer diameter in the direction perpendicular to the axis of the second bore 10b which is basically identical to the inner diameter of the second bore 10b. The head receiving member is formed of two shells 131a, 131b being arranged in the direction of the axis of the bore 10 and enclosing a cavity 133 having basically the shape of a sphere elongated in the direction of the axis of the bore 10. In the facing surfaces of the shells 131a and 131b bores 132a and 132b, having a diameter increasing from the cavity 133 toward the facing surface and being larger than the cross-section of the core 130 are provided coaxially to the second bore 10b.

The outer diameter of the core 130 is considerably smaller than the inner diameter of the bore 10. The end of the core 130 facing the rigid section 8 is provided with a cylindrical threaded projection 137, the external thread cooperating with an internal thread 138 in a bore provided in a head member 134. The head member 134, shown in FIG. 20b, consists of two essentially spherical halves 134a and 134b having in the mounted state a basically spherical outer surface having a diameter larger than the smallest diameter of the bore 132b and smaller than the smallest diameter of the cavity 133. The two essentially, spherical halves 134a and 134b cooperate as nut and lock-nut The free end 137 of the core 130 provided with the external thread is passed through the bore 132b and screwed into the head member 134 arranged in the cavity 133.

The other free end of the core 130 is accommodated in the rigid section 7 in a similar way. Depending on how far the head members 134 are screwed onto the two opposite free ends of the core 130, the head members 134 abut the inner sides of the receiving members 131 facing the bore 10, abut the inner sides facing the free ends of second bores 10a, 10b or have tolerance to these inner sides, respectively.

In his embodiment, due to the spherical shape of the head members 134 in cooperation with the basically spherical shape of the head receiving members 131, the head members 134 are allowed to slide in the head receiving members 131. Thereby, when an external flexural load acts, a flexural load acting on the core is prevented for small deflections. By screwing the head members 134 to abut the core side inner surfaces of the head receiving member 131 or the inner surfaces of the head receiving member 131 facing away from the core, respectively, a tensile strengthening and a compression strengthening, respectively, can be achieved for the rod-shaped implant element. By setting the tolerance on both sides of the head members 134 in the head receiving members 131, it can be controlled that the core is effective only when a predetermined lengthening or shortening of the outer section of the rod-shaped implant member has occurred.

FIGS. 19a to 19c and 20a show exemplary that the head receiving members 131 are fixed in the second bores 10a, 10b by screws 135 but, for fixation, it is also possible to provide screws screwed in from the side, as in the other embodiments, or to provide press-fitting of the head receiving members in the second bores, for example.

The invention has been described in detail including the preferred embodiments. However, it should be understood that those skilled in the art, upon consideration of the specification and drawings, may make modifications and improvements within the spirit and scope of the present invention. Combinations of parts of the described embodiments are possible and such combinations are specifically contemplated. Various combinations can readily be made by those skilled in the art. Further, a rigid section for cooperation with a bone anchoring element also can include a helical groove as long as it is substantially rigid relative to the flexible section and it can be fixed into a bone anchoring element. For example, the rod-shaped implant element can be made by forming a helical groove along the entire length of the rod and boring out a center coaxial bore hole. Then, a core can be inserted into a free end forming a rigid section, although an adjacent section without the core is flexible.

What is claimed is:

1. An elongated rod-shaped implant element for connecting at least two bone anchoring elements, each of which comprise an anchoring section to be anchored in the bone and a receiver member to be connected to the rod-shaped implant element, the elongated rod-shaped implant element comprising:
   a longitudinal axis and an outer surface;
   a first length of a rigid section extending along the longitudinal axis that is configured to cooperate with and be received in the receiver member;
   a second length of a flexible section extending along the longitudinal axis adjacent to the rigid section, the second length having a helical slotted opening in the outer surface of the rod-shaped implant element, the slot extending radially inward, wherein the first length of the rigid section and the flexible section are a continuous one-piece element
   a third length of a rigid section extending along the longitudinal axis, wherein the flexible section has two opposite ends, the first length of rigid section being adjacent one end and the third length of rigid section being adjacent the opposite other end; and
   a core within the flexible section and extending along substantially the entire second length of the flexible section.

2. The rod-shaped implant element according to claim 1, further defining a bore along the longitudinal axis and wherein the core is removably secured within the bore.

3. The rod-shaped implant element according to claim 1, wherein the bore comprises a coaxial longitudinal bore extending throughout the element.

4. The rod-shaped implant element according to claim 1, wherein the flexible section has a first diameter and the rigid section has at least at one point a second diameter different from the first diameter.

5. The rod-shaped implant element according to claim 1, wherein the flexible section has two symmetrical concave surfaces in the outer surface, the concavity being an arcuate shape the arc of which extends along the longitudinal axis.

6. The rod-shaped implant element according to claim 1, wherein the flexible section has an outer diameter that varies along a length of the flexible section.

7. The rod-shaped implant element according to claim 1, wherein the flexible section comprises a first material and the core comprises a second material.

8. The rod-shaped implant element according to claim 1, wherein the core has at least in a part of the flexible section a cross section with an anisotropic shape.

9. The rod-shaped implant element according to claim 1, wherein the core is accommodated in the bore with a tolerance in direction of the longitudinal axis.

10. A stabilization apparatus for bones comprising:
at least two bone anchoring elements and a rod-shaped implant element connecting the bone anchoring elements,
each bone anchoring element comprising a bone anchoring section to be anchored to the bone and a receiver member for receiving the rod-shaped implant element, and the rod-shaped implant element comprising:
a bore along a longitudinal axis and an outer surface;
at least one first length of a rigid section that is configured to cooperate with and be received in the receiver member, the bore extending along the longitudinal axis into the rigid section;
a second length of a flexible section adjacent to the rigid section, the second length having a helical slotted opening in the outer surface of the rod-shaped implant element, the slot extending radially inward, wherein the rigid section and the flexible section are a continuous one-piece element, the bore extending along the longitudinal axis into the flexible section; and
a core removably secured within the bore of the rigid section and the bore of the flexible section.

11. The stabilization apparatus for bones according to claim 10, wherein at least one of the bone anchoring elements is a monoaxial or a polyaxial bone screw.

12. A method for the production of a rod-shaped implant element having a flexible section, the method comprising the following steps:
providing a rigid rod having a longitudinal axis and an outer surface and having a free end that is configured to cooperate with and be received in a receiver member of a bone anchoring element;
producing a helical slotted opening in at least one section of the outer surface of the rod at a predefined distance from the free end of the rod, the slot extending radially inward, thereby providing a flexible section, wherein the free end and the flexible section are a continuous one-piece element;
producing a longitudinal bore extending along the longitudinal axis into the free end of the rod and throughout the flexible section; and
inserting and removably securing a core within the bore of the rigid section and the bore of the flexible section, the core extending alone substantially the entire flexible section.

13. The method according to claim 12, wherein the slotted opening is produced by a cutting process.

14. The method according to claim 12, further comprising removing a defined region of material in a longitudinal direction from the flexible section to produce a concave section that has a non-circular cross-section in at least one region of the flexible section.

15. The method according to claim 12, further comprising reducing the diameter of the rigid section as compared with the flexible section.

16. The method according to claim 12, further comprising reducing the diameter of the flexible section as compared with the rigid section.

17. A method for stabilizing vertebrae, the method comprising:
providing a stabilization apparatus for bones comprising at least two bone anchoring elements and a rod-shaped implant element connecting the bone anchoring elements, each bone anchoring element comprising a bone anchoring section to be anchored to the bone and a receiver member for receiving the rod-shaped implant element, and the rod-shaped implant element comprising:
a bore along a longitudinal axis and an outer surface;
at least one first length of a rigid section that is configured to cooperate with and be received in the receiver member, the bore extending along the longitudinal axis into the rigid section;
a second length of a flexible section adjacent to the rigid section, the second length having a helical slotted opening in the outer surface of the rod-shaped implant element, the slot extending radially inward, wherein the rigid section and the flexible section are a continuous one-piece element, the bore extending along the longitudinal axis into the flexible section; and
a core removably secured within the bore of the rigid section and the bore of the flexible section;
fixing one bone anchoring element to each of at least two vertebrae; and
inserting the rod-shaped implant element into the receiver member of each respective bone anchoring element and fixing the rod-shaped implant element therein.

18. The method according to claim 17, wherein the flexible section of the implant element is positioned substantially between two adjacent vertebrae.

19. The method according to claim 17, wherein a plurality of bone anchoring elements are fixed in a plurality of vertebrae and the implant element extends between the plurality of bone anchoring elements, and further wherein a rigid section of the implant element extends between a first vertebrae and second vertebrae and a flexible section of the implant element extends between a subsequent pair of adjacent vertebrae.

20. The method according to claim 17, wherein the flexible section of the implant element is positioned in a non-stressed state when an invertebral disk between the two vertebrae is not under stress.

21. The method according to claim 17, wherein the flexible section of the implant element is positioned in a compressed state when an invertebral disk between the two vertebrae is not under stress, to provide distraction of the vertebrae.

22. A method for stabilizing a broken or fractured bone, the method comprising:
providing a stabilization apparatus for bones comprising at Least two bone anchoring elements and a rod-shaped implant element connecting the bone anchoring elements, each bone anchoring element comprising a bone anchoring section to be anchored to the bone and a receiver member for receiving the rod-shaped implant element, and the rod-shaped implant element comprising:
a bore along a longitudinal axis and an outer surface;

at least one first length of a rigid section that is configured to cooperate with and be received in the receiver member, the bore extending along the longitudinal axis into the rigid section;

a second length of a flexible section adjacent to the rigid section, the second length having a helical slotted opening in the outer surface of the rod-shaped implant element, the slot extending radially inward, wherein the rigid section and the flexible section are a continuous one-piece element, the bore extending along the longitudinal axis into the flexible section; and a core removably secured within the bore of the rigid section and the bore of the flexible section;

fixing one bone anchoring element to a first portion of bone on one side of the break or fracture and fixing a second bone anchoring element to a second portion of bone on another side of the break or fracture; and inserting the rod-shaped implant element into the receiver member of each respective bone anchoring element and fixing the rod-shaped implant element therein.

* * * * *

UNITED STATES PATENT AND TRADEMARK OFFICE
CERTIFICATE OF CORRECTION

| | |
|---|---|
| PATENT NO. | : 7,621,912 B2 |
| APPLICATION NO. | : 10/966921 |
| DATED | : November 24, 2009 |
| INVENTOR(S) | : Harms et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1120 days.

Signed and Sealed this

Twenty-sixth Day of October, 2010

David J. Kappos
*Director of the United States Patent and Trademark Office*